United States Patent [19]
Brochot et al.

[11] Patent Number: 5,081,014
[45] Date of Patent: Jan. 14, 1992

[54] METHOD OF MEASURING A CO-ENZYME

[75] Inventors: Jean Brochot, Julien-en Genevois, France; Iqbal Siddiqi, Geneva, Switzerland

[73] Assignee: Hoffmann-La Roche Inc., Nutley, N.J.

[21] Appl. No.: 587,480

[22] Filed: Sep. 19, 1990

Related U.S. Application Data

[63] Continuation of Ser. No. 294,929, Jan. 5, 1989, abandoned, which is a continuation of Ser. No. 942,104, Dec. 16, 1986, abandoned.

[30] Foreign Application Priority Data

Dec. 23, 1985 [CH] Switzerland .................... 5502/85

[51] Int. Cl.$^5$ .................... C12Q 1/58; C12Q 1/54; C12Q 1/52; C12Q 1/34
[52] U.S. Cl. .................................... 435/12; 435/14; 435/16; 435/18; 435/26; 435/28
[58] Field of Search .................. 435/12, 14, 15, 26, 435/28, 16, 18

[56] References Cited

U.S. PATENT DOCUMENTS 4,271,265 6/1981 Deneke et al. .................... 435/16
4,353,983 10/1982 Siddiqi .................... 435/11

FOREIGN PATENT DOCUMENTS

| | | |
|---|---|---|
| 0029104 | 5/1981 | European Pat. Off. . |
| 0034213 | 8/1981 | European Pat. Off. . |
| 0124909 | 11/1984 | European Pat. Off. . |
| 0135092 | 3/1985 | European Pat. Off. ............ 435/12 |
| 0175898 | 10/1984 | Japan .................... 435/16 |
| 0149399 | 8/1985 | Japan .................... 435/16 |

OTHER PUBLICATIONS

The Merck Index, Tenth Edition, 1983, p. 762.
White-Stevens et al., J. Biol. Chem., vol. 247, 1972, pp. 2358.

*Primary Examiner*—Esther L. Kepplinger
*Assistant Examiner*—Jacintha M. Stall
*Attorney, Agent, or Firm*—George M. Gould; George W. Johnston; Alan P. Kass

[57] ABSTRACT

The method makes use of the action of the co-enzyme in the production of $H_2O_2$ associated with the reaction of a hydroxylase with a decoupling agent in the presence of air or oxygen, the $H_2O_2$ being subsequently determined by quantitative breaking of the C—F bond of a fluorinated compound in the presence of peroxidase, followed by electrometric titration of the resulting ions.

7 Claims, 1 Drawing Sheet

METHOD OF MEASURING A CO-ENZYME

This is a continuation of copending application Ser. No. 07/294,929 filed on Jan. 5, 1989 now abandoned which is a continuation of copending application Ser. No. 06/942,104, filed on Dec. 16, 1986, now abandoned.

BACKGROUND OF THE INVENTION

The invention relates to biological analysis, and more particularly, to a method of determining the presence of and measuring the amounts of the co-enzymes NADH and NADPH.

As is known, the aforementioned abbreviations denote the following substances:
NADH = reduced form of NAD (or $NAD^+$) (nicotinamide-adenine dinucleotide), also called co-enzyme I or DPN (diphosphopyridine nucleotide)
NADPH = reduced form of NADP (or $NADP^+$) (nicotinamide-adenine-dinucleotide phosphate), also called co-enzyme II or TPN (triphosphopyridine nucleotide).

The reversible conversion of NAD into NADH is shown diagrammatically as follows (where R denotes a ribose-diphosphate-ribose-adenine chain):

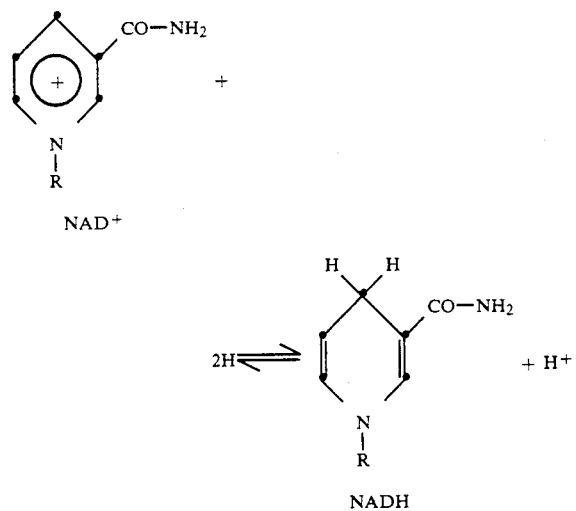

The aforementioned enzymes play a part in a large number of biochemical enzymatic reactions used as clinical tests. One example of these reactions is oxidation of α-hydroxyacids into corresponding ketonic acids in the presence of a suitable dehydrogenase. One example is the oxidation of lactic acid or lactates to pyruvic acid, which is represented as follows:

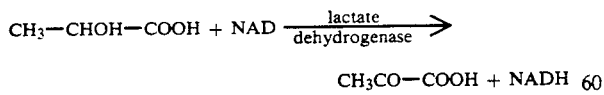

$$CH_3CO-COOH + NADH$$

Similarly, glucose-6-phosphate is oxidized in the presence of NADP and glucose-6-phosphate dehydrogenase (G6PDH) to glucoma-δ-lactone-6-phosphate and NADPH. The determination of NADP or NADH in an aforementioned reaction is very important, since it can be indirectly used for determining glucose in biological fluids after they have been converted into glucose-6-phosphate in the presence of ATP (adenosine triphosphate) and hexokinase (HK).

NADH also acts as a co-enzymatic factor in the conversion of 2-oxoglutarate into L-glutamate by ammonium salts in the presence of GLDH (glutamate dehydrogenase), thus enabling the ammonium in the reaction medium to be determined by measuring the $NADH^+$ formed. This can be used for determining urea in biological fluids, since urea in the presence of urease supplies $NH_3$ which occurs as the $NH^+_4$ ion in the aforementioned conversion.

Similarly, the determination of transaminase in blood serum which catalyzes the conversion of α-ketoglutarate into oxaloacetate (SGOT = serum glutamate oxaloacetate transaminase) is very important in clinical chemistry, since an excess of this enzyme can indicate a coronary thrombosis.

Measurement of SGOT is associated with measurement of the reduction of the oxaloacetate formed during the aforementioned reaction by NADH in the presence of malate dehydrogenase (MDH) or glutamate dehydrogenase (GLDH). The reaction diagram is as follows:

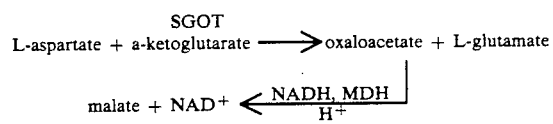

A description of other applications associated with the determination of the $NAD^+$ and NADH factors are found in the following documents: EP-A-29 104 (MILES); FR-A-2 299 644 (AKZO).

In view of the importance of determining the aforementioned co-enzymes in one or the other of their states of oxydo-reduction, numerous techniques have been proposed for this purpose.

For example, since NAD and NADH have different absorptions in the UV range of the spectrum, one form can be determined in the presence of the other by spectrophotometry. The sensitivity of spectrophotometric determination can also be amplified by combined use of colored redox compounds, for example tetrazolium compounds which form intensely colored formazan salts in the presence of NADH or NADPH and an electron acceptor such as phenazine methosulphate (See, for example, document EP-A-114 267). Alternatively, use may be made of fluorimetric techniques as described, for example, in document FR-A-2 266 644.

Alternatively, an electrochemical method may be used as described in document JP 56 035 50. where NADH or NADPH is oxidized with Meldola blue, after which the reduced form of the dye is electrochemically oxidized and the oxidation current is measured.

The following reaction has recently been recommended (see R. H. WHITE-STEVENS et al., J. Biol. Chem. (1972) 247. 2358; EP-A-29 104):

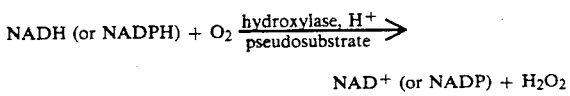

$$NAD^+ (or\ NADP) + H_2O_2$$

The thus-liberated hydrogen peroxide ($H_2O_2$) is then determined by conventional means, for example, by its action, catalyzed by peroxydase, on a redox indicator, the oxidized form of which is determined by colorimetry.

This technique is very attractive but is of use only in a colorless, optically transparent medium, which is far from being the case with most biological fluids used for analysis. Also, in operation this technique requires the presence of a "coupler" for preventing the dyed oxidized compound from being reversibly reduced by NADH in the analysis medium. In order to determine $H_2O_2$ under these conditions, it is therefore desirable to have a technique supplying identifiable products in an irreversible manner. With regard to these techniques, it has recently been disclosed (see EP-A-20 623) that excellent results with regard both to sensitivity and accuracy can be obtained in the analysis of $H_2O_2$ produced by oxidation of glucose in the presence of glucose oxidase, the method involving reacting the $H_2O_2$ with an aromatic fluorinated compound in the presence of peroxidase so as to liberate fluoride ions, which are then electrometrically determined by using an electrode specific to these ions.

DESCRIPTION OF THE INVENTION

It has now been surprisingly discovered that a new technique is useful for determining NADH or NADPH co-enzymes, and this discovery forms the basis of the present invention. Briefly, the present invention provides a method of measuring the amount of NADH or of NADPH in a biochemical analysis system containing either of these co-enzymes in reduced form or in oxidized form, which method comprises oxidizing the NADH or NADPH by contacting with air or oxygen in a buffered medium at a controlled pH and ionic strength, in the presence of monooxygenase salicylate hydroxylase enzyme and a decoupling agent, to form hydrogen peroxide ($H_2O_2$) in proportion to the amount of NADH or NADPH present, then reacting the $H_2O_2$ thus formed with a fluoroaromatic compound in the presence of a peroxidation agent whereby the fluoroaromatic compound is catalytically and irreversibly oxidized, breaking the C-F bond and forming fluoride ($F^-$) ions in stoichiometric relation to the amount of NADH or NADPH, and electrometrically titrating the $F^-$ ions thus formed. Use can be made of acetate, phosphate and cacodylate buffers over a pH range from about 5 to 8 and an ionic strength of 0.1 to 1. A cacodylate buffer at pH 7.5 and ionic strength of 0.1 to 0.5 are preferably used.

The fluoride ion liberated by this method is preferably determined by the electrometric method as disclosed in document EP-A-20 623. However, any method based on use of another electrode selective to fluoride ions will be equally suitable.

The general principle of the present method can be briefly described as follows: The invention is based on a system whereby a buffer medium of given ionic strength and pH containing the reduced co-enzyme to be determined is mixed with an excess of a "decoupling" pseudo-substrate, for example, sodium benzoate, and the enzyme monooxygenase salicylate hydroxylase (SH) which, in the presence of NADH (or NADPH), catalyzes the reduction of the oxygen present to hydrogen peroxide. The amount of hydrogen peroxide formed is proportional to the amount of NADH for analysis. In the presence of an excess of a fluorinated aromatic compound and a peroxidation agent such as peroxidase (HRP or POD), an irreversible break occurs in the C-F bond of the fluorinated compound, with corresponding liberation of $F^-$ ions at a reaction rate proportional to the quantity of enzyme present. There is also a stoichiometric relation between the aforementioned quantity of liberated fluoride ions and the quantity of co-enzyme to be determined. From the analytical viewpoint, however, this relation is less interesting since the reaction quickly slows down after a vigorous beginning and it is impracticable to make "end-point" type measurements. However. "fixed-time" analyses may be made by determining the reagents after a given time, always the same, in a set of similar analytical operations. In general, however, it is preferable to measure the liberation rates of $F^-$ ions under highly standardized conditions in order to ensure good reproducibility of measurements. For example, the gradients of the rate curves (which of course depend on certain reaction parameters as well as the concentration of substance to be measured) are advantageously measured after a certain latency time, which is usually kept constant during a set of comparative tests. However, the latency time may differ slightly from one analysis to the other, the maximum rate being reached more quickly with increasing NADH concentration.

Preferably, the concentration of liberated $F^-$ ions is determined by using an electrode sensitive to $F^-$ ions but inert towards other types of ions. The preferred type of electrode is a type 96-09 electrode selective to $F^-$ ions and produced by ORION RESEARCH INC.. CAMBRIDGE. MASS. However, other electrodes may be equally suitable. All details regarding use of these electrodes for determining $F^-$ ions may be found in the aforementioned document EPA-20 623.

When the present reaction medium is used for determining precursor systems, that is, systems where the quantitative formation of the co-enzyme depends on one or more successive transformations of a substance to be measured, the technique to be applied is very similar to that described hereinbefore. The reason (and this is one of the significant advantages of the invention) is that the detection and electrochemical measurement of fluoride ions is unaffected by the presence of numerous other factors and dissolved substances in the reaction medium. The present process is also directly useful for measuring glucose and urea by procedures similar to those mentioned in the introduction.

Glucose, for example, is determined by first converting it to glucose-6-phosphate in the presence of ATP and hexokinase (or another enzyme having similar properties). Next, since the medium contains a known quantity of NAD. the previously-mentioned process is used to measure the NADH formed during conversion of glucose-6-phosphate to glucoma-δ-lactone-6-phosphate in the presence of G6PDH. At the start of the reaction, the reaction medium does not contain NADH, which appears during the enzymatic process. Actually the three reactions, that is, the one catalyzed by hexokinase, the one catalyzed by G6PDH and the one catalyzed by hydroxylase, occur simultaneously in the presence of NADH and ATP. Accordingly the formation of NADH is continuously measured from the beginning of the reaction and the rate constant of this reaction is the critical factor. Similar considerations apply to all other biochemical reactions involving the present co-enzymes either as the starting products or as reaction products. The determination of urea is an example.

A sample of urea taken from a biological fluid, for example, urine or blood plasma, and mixed with a suitable buffer, is mixed with an excess of urease, oxoglutarate and GLDH accompanied by an exactly known quantity of NADH (also in excess but of the same order as the urea to be measured, to avoid problems of disproportion). Next, after waiting for a given time for transformation of NADH into NAD+ to occur, the fluorinated compound, benzoate and hydroxylase are added, the F− ion electrode is inserted into the mixture and the mixture is agitated in air. A catalytic quantity of peroxidase (POD) is added and the variation in electrode potential with time is measured in order to determine the quantity of NADH not used in the reaction and thus deduce the quantity of urea in the analyzed sample.

Document EP-A-20 623 gives details of the operating technique using the fluorine electrode and also sets out the physico-chemical considerations when interpreting the results.

In short, the liberation rate of F− ions after reaction of an unknown sample is determined preferably by referring to a calibration curve. A calibration curve can be obtained as previously described by determining a set of samples containing known concentrations of co-enzyme. The rate of liberation of F− ions is recorded for each sample and the gradient of the kinetic curves is measured at a time (the same of course for each sample) when the rate curves are almost straight. Next, the values of the gradient are graphically recorded in dependence on the concentrations of co-enzyme so as to obtain a standard reference curve. The measured electrometric parameters used for preparing the kinetic curves can be the recorded voltages of the electometric system used in combination with the fluorine electrode (mV) or, preferably, the corresponding values of [F−] which can be calculated by the Nernst equation, which in the present case has the following form:

$$E = E' - S \cdot Log\ [F^-]$$

wherein E is the measured voltage and E' is an experimentally-determined constant belonging to the system and including the activity factors and the liquid-junction potentials. S is the "Nernst gradient" and is a constant equal to about 57.5 mV (in the cacodylate buffer at pH 7.5) for a variation of 10 units in the concentration of F− ions, the concentration being expressed in mols/l. If the values of [F−] calculated from the above relation are used in the rate graphs instead of the values in mV. the resulting curves are very close to straight lines, the gradient of which is easier to determine and results in more accurate reference graphs.

The following are preferred fluorinated aromatic compounds suitable for the practice of the invention: 4-fluoroaniline, 4-fluorophenol, 2,3,5,6-tetrafluorophenol and pentafluorophenol. It is preferred to use 2-fluorophenol and the aforementioned tetra-and pentafluoro derivatives.

The invention is illustrated in greater detail by the following examples, which will be more clearly understood by referring to the accompanying drawings in which.

EXAMPLE I

Determination of NADH

A buffer solution was used for this determination according to the invention. Preferably, a conventional cacodylate buffer at pH 7.5 is used. 21.4 g of sodium dimethylarsinate trihydrate (MERCK) were dissolved in 800 ml of twice-distilled water and 2 ml of a $10^{-3}$ M solution of NaF were added (traces of NaF are added to reaction mediums in order to stabilize the base potential of the fluorine electrode). The pH was adjusted to 7.5 (1 N HCl) and the mixture was made up to 1 liter with twice-distilled $H_2O$.

Reaction medium

The operating medium in the aforementioned buffer was prepared by dissolving the following reagents in the following molar concentrations: 0.01 M p-fluorophenol; 0.03 M sodium benzoate; 2 U/ml horse-radish peroxidase (HRP); 0.11 U/ml salicylate hydroxylase, and 3 μM NaF.

Standard solution of NADH

In the aforementioned cacodylate buffer, a stock solution of $5 \times 10^{-2}$ M NADH was prepared by dilution of the commercial reagent (SIGMA). Next, using the same buffer, the following standard solutions were prepared by dilution: $2.5 \times 10^{-2}$ M; $10^{-2}$ M; $5 \times 10^{-3}$ M and $2 \times 10^{-3}$ M.

Method of operation 4.9 ml of the aforementioned reaction medium were poured into a 10 ml polyethylene beaker and an electrode specifically sensitive to F− ions (Type Orion 96-09, ORION RESEARCH CO., Cambridge, Mass.) comprising an internal reference electrode was immersed in the liquid with magnetic agitation. The electrode was connected to a very sensitive commercial electrometer (KEITHLEY ELECTROMETER, Type 619. Cleveland, Ohio).

The device was switched on and left to stabilize for 3 minutes at ambient temperature, after which 0.1 ml of one of the aforementioned standard solutions was added and the liberation rate of F− ions by the aforementioned reaction was measured for about 2 minutes by recording the corresponding electrode potential. The recorded data were also transmitted to a computer which supplied the gradient of the rate curve in its linear region (after about 20 seconds and for 30 seconds to 1 minute). these parameters of course were kept constant during the entire calibration phase and for subsequent analysis of unknown samples, which was done in identical manner.

Figure 1:
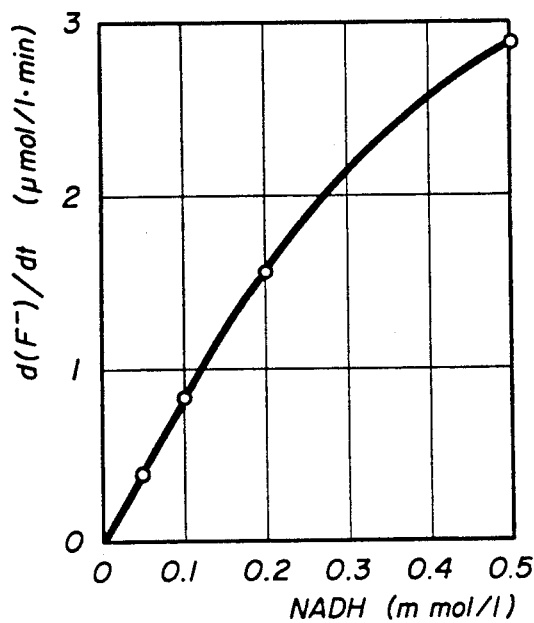
FIG. 1 is a graph showing the variation in the amount of NADH with the rate of liberation of F− ions.

The results are shown graphically in FIG. 1. The graph shows the variation in liberation rates of F− ions in μmols/l/min (μmols/l.min) in dependence on the molar concentration of NADH in the analyzed medium.

Unknown solutions of NADH were analyzed in identical manner and the molar concentration of NADH in the operating medium was determined by comparing the measured kinetic value with the graph in FIG. 1.

EXAMPLE 2

Analysis of SGOT

Reagent A

A solution was prepared in the cacodylate buffer described in the preceding example (pH 7.5) using the following ingredients in the following molar concentrations: 4-fluorophenol 0.012 M (1.345 g/l); sodium benzoate 0.037 M (5.33 g/l); L-aspartic acid 0.26 M (34.609 g/l).

Reaction medium

This solution was prepared by using reagent A as a solvent and a solution of NADH in the aforementioned 0.1 M cacodylate buffer (NADH 50 mM. (38 g/l). Use was also made of reagents from the ROCHE (DIAGNOSTICA) kit present in the form of portions each containing malate dehydrogenase (MDH) enzyme and lactate dehydrogenase (LDH) enzyme and a small proportion of NADH. This kit, called "GOT OPT., DGKC". is described in the corresponding operating instructions (List No 07 14410 [10×10 ml]) and contains bottles holding the following portions: NADH 2.3 mol. LDH 0.26 μkat=15.6U. MDH 0.13 μkat=7.8 U (1 μkat=60 U). The presence of LDH is due to the fact that the kit is intended for analysis of SGOT in serum. Serum contains pyruvate which has to be enzymatically decomposed beforehand so that it does not interfere with the measurement of SGOT.

In order to prepare the present solution. 1.9 μmols of NADH, that is, 40 μl of the aforementioned 50 mM NADH solution, were added to the contents of a bottle in the kit and the mixture was dissolved in 10 ml with reagent A. The solution was therefore 0.42 mM NADH and contained 1600 U LDH and 800 U MDH per liter.

Standard samples of SGOT

The reagent used was GOT-CALBIOCHEM, 2180 IU/ml, comprising a 3.2 M solution of ammonium sulphate, 2.5 mM of 2-oxoglutarate and 50 mM of sodium malate. The reagent was first diluted at 1/150 with water, and the dilution was re-diluted at 1/97 with the aforementioned cacodylate buffer. The resulting solution contained 0.15 U/ml and was used to prepare the following standards: (b) 30 U/l; (c) 60 U/l; (d) 90 U/l. A control (a) without SGOT was also prepared by correspondingly diluting a solution of 3.2 M $(NH_4)_2DO_4$, 2.5 mM 2-oxoglutarate and 50 mM sodium malate.

Reagent B

The solution was prepared from 0.1 M cacodylate buffer and contained 6 U of salicylate hydroxylase (SH) and 100 U of HRP per ml.

Method of operation

Figure 2:
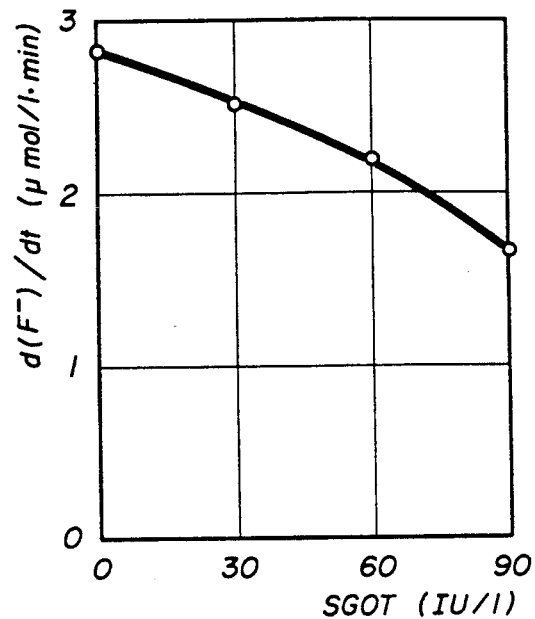
FIG. 2 is a graph similar to FIG. 1, but relating to the analysis of SGOT.

The procedure was as in Example 1. 3.2 ml of reaction solution, 0.6 ml SGOT standard and 0.1 ml of an aqueous 468 mM solution of 2-oxoglutarate were pipetted into a 10-ml beaker. The reaction was then allowed to occur for 12 minutes under agitation at ambient temperature, after which the fluoride electrode was immersed therein. The mixture was left to stabilize for exactly 3 minutes and 0.1 ml of reagent B was added, resulting in formation of $H_2O_2$ in proportion to the NADH remaining to be determined, and the liberation rate of $F^-$ was measured. The results are given in a graph in FIG. 2, showing the decrease in the $F^-$ liberation rate (in μmols/l.min of $F^-$) with respect to the increase in SGOT in the titrated sample. The resulting curve was of subsequent use in determining unknown samples of SGOT, inter alia blood serum.

EXAMPLE 3

Determination of glucose

The following reagents and solutions were prepared:

A: Cacodylate buffer

Sodium benzoate 0.03 M (216 mg/50 ml); 4-fluorophenol 10 mM (56 mg/50 ml); NaF $3 \times 10^{-6}$ M (0.15 ml of $10^{-3}$ M/50 ml sol); twice-distilled water.

B: Reaction medium

The contents of a bottle of "Reagent 1" from the "Glucose Rapid Test (ROCHE)" glucose-measuring kit, list No 07 1100 4, was dissolved in 24.5 ml of buffer A. The bottle contained the following products:

| | |
|---|---|
| ATP (adenosine triphosphate) | 50 μmol; |
| $NAD^+$ | 50 μmol |
| HK (hexokinase) | >7 U |
| G6-PDH (Glucose-6-phosphate dehydrogenase) | 8 U. |

The resulting solution had the following molar concentration:

ATP $2.04 \times 10^{-3}$ M; $NAD^+$ $2.04 \times 10^{-3}$ M; HK 0.286 U/ml; G6-PDH 0.326 U/ml.

C: The following enzymes were dissolved in the following proportions in buffer A: POD (Peroxidase) 0.4 mg/ml (100 U/ml); salicylate hydroxylase (SH) 2.5 mg/ml (5.75 U/ml).

D: Standard glucose solutions: in a 0.1% solution of benzoic acid, standard glucose solutions were prepared at the following concentrations in g/l: 50, 100, 200, 300 and 400.

Method of operation

The method was similar to that described in the previous Examples except that the present analysis consisted in determining NADH as soon as formed by reduction of $NAD^+$. Consequently, there was no waiting period, unlike the previous cases.

3.8 ml of reaction solution B and 0.1 ml of solution C were used. The electrode was immersed in the medium and, after stabilization for 3 minutes, 0.1 ml of the standard glucose solution was added and measurements were made for 1 to 2 minutes.

The gradient of the rate curves as obtained by the computer is shown hereinafter in dependence on the concentration of the standard glucose solutions:

| Glucose solution (g)l | Speed (μmol $F^-$/l. min) |
|---|---|
| 0 | 0.074 |
| 0.5 | 0.361 |
| 1 | 0.610 |
| 2 | 0.963 |
| 3 | 1.176 |
| 4 | 1.328 |

Figure 3:
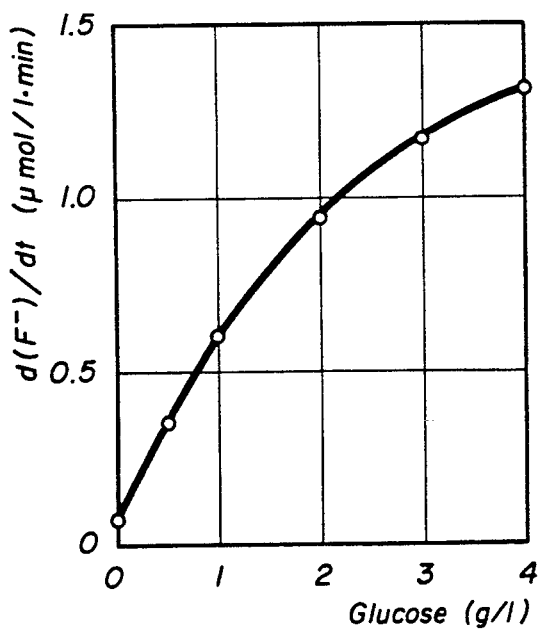
FIG. 3 is a graph similar to FIG. 1, but relating to the analysis of glucose.

These values are shown in the graph in FIG. 3, which was then used as a reference curve for determining unknown glucose solutions.

EXAMPLE 4

Determination of urea

The following solutions and reagents were prepared:

A: Cacodylate buffer: identical with that in Example 3.

B: Reaction medium: use was made of the reagents supplied by Roche in the urea UV test (ROCHE) kit, list No. 07 13228. Reagent (1) contains the following per portion: urease >25 U; 2-oxoglutarate 197 μmols; NADH 6 μmols. Two of the aforementioned portions were dissolved in 50 ml of buffer A, after which 200 μl were added from the glutamate dehydrogenase solution (about 60 U GLDH) from portion 3 in the ROCHE kit and 250 μl of a $5 \times 10^{-2}$ M NADH solution in buffer A (38 mg/ml).

C: Enzyme solution: this contained 0.4 mg/ml POD and 2.5 mg/ml SH in buffer A.

D: Standard urea sample

These samples were obtained by diluting a 7.13 mM stock solution in water.

| | |
|---|---|
| 0.04 ml stock + 0.16 ml $H_2O$ | 1.43 mols |
| 0.08 ml stock + 0.12 ml $H_2O$ | 2.85 mols |
| 0.12 ml stock + 0.08 ml $H_2O$ | 4.28 mols |
| 0.2 ml stock | 0.0 |

Method of operation

Figure 4:
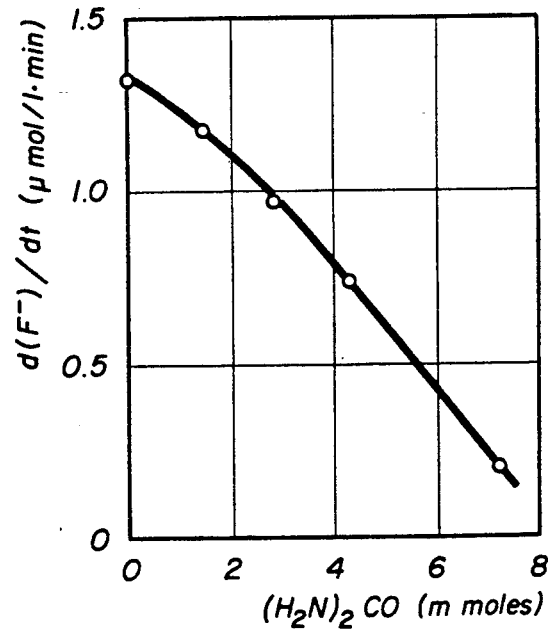
FIG. 4 is a graph similar to FIG. 1, but relating to the analysis of urea.

The procedure was as follows:

3.7 ml of reagent solution B followed by 0.2 ml of urea sample were poured into a mechanically agitated beaker. The reaction was then allowed to continue for exactly 12 minutes, after which the fluorine electrode was immersed and, after 3 minutes of stabilization. 0.1 ml of solution C was added The liberation rate of $F^-$ was then measured for 1 to 2 minutes and the gradient of the rate curve was determined. The results are shown hereinafter, and also in the Table in FIG. 4.

| Urea Sample | Speed (μmols $F^-$/l. min) |
|---|---|
| 0 (control) | 1.32 |
| 1.43 | 1.18 |
| 2.85 | 0.99 |
| 4.28 | 0.76 |
| 7.13 | 0.22 |

The resulting values were then used to measure the urea content of unknown samples, by comparison.

We claim:

1. A method of measuring the amount of the coenzyme NADH or the co-enzyme NADPH present in a biochemical analysis system, which method comprises oxidizing the coenzyme with air or oxygen in a buffer medium at a controlled pH and ionic strength in the presence of monooxygenase salicylate hydroxylase and a benzoate decoupling agent, whereby $H_2O_2$ is formed in proportion to the quantity of the NADH or NADPH present, reacting the $H_2O_2$ thus formed with a fluoroaromatic compound selected from the group consisting of 4-fluoroaniline, 4-fluorophenyl, 2,3,5,6-tetrafluorophenol and pentafluorophenol in the presence of a peroxidase, whereby the fluoroaromatic compound is catalytically and irreversibly oxidized, the C—F bond in said compound is broken and fluoride ions ($F^-$) are formed in proportion to the quantity of NADH or NADPH present, and electrometrically titrating the $F^-$ ions thus formed using an electrode which is selectively sensitive to $F^-$ ions.

2. A method according to claim 2, wherein the buffer is a phosphate, acetate or cacodylate buffer, at a pH of 6 to 8 and an ionic strength of 0.1 to 0.5.

3. A method according to claim 2, wherein the buffer is 0.1 M cacodylate having a pH of 7.5.

4. A method according to claim 1, in which the benzoate is sodium benzoate.

5. A method according to claim 1, in which said biochemical analysis system comprises NADH in a known amount, serum glutarate oxaloacetate transaminase (SGOT), α-ketoglutarate and L-aspartate in which the SGOT catalyzes the reaction of the α-ketoglutarate with the L-aspartate into oxaloacetate and the oxaloacetate is converted into malate by reduction with the NADH, said method comprising measuring the amount of unreacted NADH in said system, and calculating from said amount the amount of SGOT.

6. A method according to claim 1, in which said biochemical analysis system comprises glucose, ATP, hexokinase, a known amount of nicotinamide-adenine dinucleotide (NAD) and glucose-6-phosphate dehydrogenase (G6PDH) in which the glucose is converted to glucose-6-phosphate in the presence of the ATP and the hexokinase, and the glucose-6-phosphate thus formed is oxidized in the presence of the NAD and the G6PDH into glucose-δ-lactone-6-phosphate with the attendant formation of NADH, said method comprising measuring the amount of NADH as it is formed, and calculating from said amount the amount of glucose.

7. A method according to claim 2, in which said biochemical analysis system comprises urea, urease, 2-oxoglutarate, glutamate dehydrogenase (GLDH) and a known amount of NADH in which the urea is converted into ammonium salts by the urease and the 2-oxoglutarate is converted into L-glutamate by the ammonium salts in the presence of the GLDH and the NADH, said method comprising measuring the amount of unreacted NADH in said system, and calculating from said amount the amount of urea.

* * * * *

UNITED STATES PATENT AND TRADEMARK OFFICE
CERTIFICATE OF CORRECTION

PATENT NO. : 5,081,014
DATED : January 14, 1992
INVENTOR(S) : Jean Brochot and Iqbal Siddiqi It is certified that error appears in the above-identified patent and that said Letters Patent is hereby corrected as shown below:

In claim 2, column 10, line 16, please delete "claim 2" and insert therefor -- claim 1 --;

In claim 6, column 10, line 41, please delete "glucose" and insert therefor -- glucono --;

In claim 7, column 10, line 45, please delete "claim 2" and insert therefor -- claim 1 --.

Signed and Sealed this

Twenty-ninth Day of June, 1993

Attest:

MICHAEL K. KIRK

*Attesting Officer*  *Acting Commissioner of Patents and Trademarks*